US012595225B2

(12) United States Patent
Park et al.

(10) Patent No.: US 12,595,225 B2
(45) Date of Patent: Apr. 7, 2026

(54) METHOD FOR PRODUCING ASYMMETRIC LINEAR CARBONATE

(71) Applicant: LG CHEM, LTD., Seoul (KR)

(72) Inventors: Jun Beom Park, Daejeon (KR); Hyunyoung Lee, Daejeon (KR); Hyun Cheol Kim, Daejeon (KR)

(73) Assignee: LG Chem, Ltd., Seoul (KR)

(*) Notice: Subject to any disclaimer, the term of this patent is extended or adjusted under 35 U.S.C. 154(b) by 447 days.

(21) Appl. No.: 18/028,184

(22) PCT Filed: Jun. 28, 2022

(86) PCT No.: PCT/KR2022/009253
§ 371 (c)(1),
(2) Date: Mar. 23, 2023

(87) PCT Pub. No.: WO2023/038249
PCT Pub. Date: Mar. 16, 2023

(65) Prior Publication Data

US 2023/0373899 A1 Nov. 23, 2023

(30) Foreign Application Priority Data

Sep. 7, 2021 (KR) ........................ 10-2021-0119070

(51) Int. Cl.
*C07C 68/06* (2020.01)
*C07C 69/96* (2006.01)

(52) U.S. Cl.
CPC .............. *C07C 68/06* (2013.01); *C07C 69/96* (2013.01)

(58) Field of Classification Search
None
See application file for complete search history.

(56) References Cited

U.S. PATENT DOCUMENTS

| | | | |
|---|---|---|---|
| 5,962,720 | A | 10/1999 | Gan et al. |
| 6,620,959 | B1 | 9/2003 | Buchanan et al. |
| 2017/0081302 | A1 | 3/2017 | Kim et al. |

FOREIGN PATENT DOCUMENTS

| | | | |
|---|---|---|---|
| CN | 110878020 | A | 3/2020 |
| CN | 111138285 | A | 5/2020 |
| JP | 1998-338663 | A | 12/1998 |
| TW | 200402415 | A | 2/2004 |
| WO | 2021-114091 | A1 | 6/2021 |

OTHER PUBLICATIONS

Machine-generated English translation of Foreign Patent Application Publication No. WO2021/114091, published Jun. 17, 2021.*
Gu, et al. (2018) "CO2 Promoted Synthesis of Unsymmetrical Organic Carbonate Using Switchable Agents Based on DBU and Alcohols" New Journal of Chemistry, 42, 15, pp. 13054-13064.
Munshi, et al. (2014) "1,8-Diazabicyclo[5.4.0]undec-7-ene (DBU): A Highly Efficient Catalyst in Glycerol Carbonate Synthesis", Journal of Molecular Catalysis A: Chemical, 391, pp. 144-149.
Liu, et al., "Versatile Imidazole-Anion-Derived Ionic Liquids with Unparalleled Activity for Alcoholysis of Polyester Wastes under Mild and Green Conditions", ACS Sustainable Chem. Eng. 2018, 6, 15127-15134.
Yang, et al., "Zeolitic imidazole framework-67 as an efficient heterogeneous catalyst for the synthesis of ethyl methyl carbonate", Catalysis Communications, vol. 54, pp. 76-90 (Sep. 1, 2014).
Song, et al., "Protic ionic liquid-promoted synthesis of dimethyl carbonate from ethylene carbonate and methanol", Chinese Chemical Letters, vol. 31, No. 3, pp. 667-672 (Jul. 27, 2019).
Zhu, et al., "DBU-Based Protic Ionic Liquids for CO2 Capture", ACS Sustainable Chemistry & Engineering, vol. 5, No. 9, pp. 8192-8198 (Sep. 5, 2017).
Qiu, et al., "Efficient Ionic-Liquid-Promoted Chemical Fixation of CO2 into [alpha]-Alkylidene Cyclic Carbonates", ChemSusChem, vol. 10, No. 6, pp. 1120-1127 (Mar. 22, 2017).
Jadhav, et al., "Room temperature ionic liquid promoted improved and rapid synthesis of highly functionalized imidazole and evaluation of their inhibitory activity against human cancer cells", Journal of the Chinese Chemical Society, Chinese Electronic Periodical Services, vol. 68, No. 6, pp. 1067-1081 (Jan. 13, 2021).
Hu, et al., "Transformation of Atmospheric CO2 Catalyzed by Protic Ionic Liquids Efficient Synthesis of 2-Oxazolidinones", Angewandte Chemie International Edition, vol. 54, No. 18, pp. 5399-5403 (Mar. 3, 2015).

* cited by examiner

*Primary Examiner* — Po-Chih Chen
(74) *Attorney, Agent, or Firm* — Bryan Cave Leighton Paisner LLP

(57) ABSTRACT

The present specification relates to a method for preparing an asymmetric linear carbonate.

8 Claims, No Drawings

METHOD FOR PRODUCING ASYMMETRIC LINEAR CARBONATE

CROSS-REFERENCE TO RELATED APPLICATIONS

This application is a National Phase entry pursuant to 35 U.S.C. § 371 of International Application No. PCT/KR2022/009253, filed on Jun. 28, 2022, and claims the benefit of and priority to Korean Patent Application No. 10-2021-0119070, filed on Sep. 7, 2021, the disclosures of which are incorporated by reference in their entirety for all purposes as if fully set forth herein.

TECHNICAL FIELD

The present specification relates to a method for preparing an asymmetric linear carbonate.

BACKGROUND

An asymmetric linear carbonate is usually used as an electrolytic solution for a lithium secondary battery, and since the asymmetric linear carbonate has excellent energy storage density, charge capacity, charge/discharge recovery, stability, and the like compared to existing electrolytic solutions, the asymmetric linear carbonate is usually used as an electrolytic solution particularly for a lithium secondary battery.

As a method for preparing an asymmetric linear carbonate, there is a method using an ester reaction of an alkyl chloroformate and an alcohol in the presence of a basic catalyst, but the method has a problem in that the ester reaction is very intense and a highly toxic compound such as phosgene and bisphenol-A needs to be used as a starting material. To complement the problem, there is a method of using a transesterification reaction of a symmetric linear carbonate and an alcohol having an alkyl group in the presence of a basic catalyst such as a metal carbonate, but the method has a problem in that catalytic activity and production yield are low, and an asymmetric linear carbonate such as ethyl methyl carbonate, which is a final target compound needs to be isolated from a total of five reaction products including three types of linear carbonates and two types of alcohols and purified. As another method, a method for preparing an asymmetric linear carbonate in the presence of moisture or alcohol using a mixed oxide of a Group 3 rare earth metal is disclosed, but there is a problem in that the method needs to be performed for a long period of time of 200 hours or more.

The background description provided herein is for the purpose of generally presenting context of the disclosure. Unless otherwise indicated herein, the materials described in this section are not prior art to the claims in this application and are not admitted to be prior art, or suggestions of the prior art, by inclusion in this section.

DETAILED DESCRIPTION OF THE INVENTION

Technical Problem

The present specification has been made in an effort to provide a method for preparing an asymmetric linear carbonate.

Technical Solution

According to an exemplary embodiment of the present specification, provided is a method for preparing an asymmetric linear carbonate, the method including: transesterifying a first symmetric linear carbonate and a second symmetric linear carbonate under a catalyst represented by Chemical Formula 1.

[Chemical Formula 1]

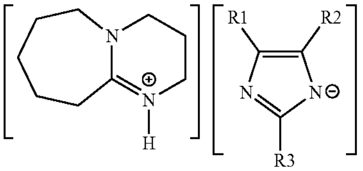

In Chemical Formula 1,

R1 to R3 are the same as or different from each other, and are each independently hydrogen; or a straight-chained or branched alkyl group having 1 to 4 carbon atoms.

Advantageous Effects

For the method for preparing an asymmetric linear carbonate according to an exemplary embodiment of the present specification, the process is simple and purification is easily performed, so that the asymmetric linear carbonate can be economically prepared.

Best Mode

Hereinafter, the present specification will be described in more detail.

According to an exemplary embodiment of the present specification, provided is a method for preparing an asymmetric linear carbonate, the method including: transesterifying a first symmetric linear carbonate and a second symmetric linear carbonate under a catalyst represented by the following Chemical Formula 1.

[Chemical Formula 1]

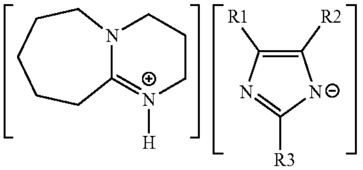

In Chemical Formula 1,

R1 to R3 are the same as or different from each other, and are each independently hydrogen; or a straight-chained or branched alkyl group having 1 to 4 carbon atoms.

In an exemplary embodiment of the present specification, a portion wherein a substituent is not indicated in Chemical Formula 1 may mean that hydrogen is substituted.

According to an exemplary embodiment of the present specification, the catalyst of Chemical Formula 1 is an ionic liquid catalyst.

According to an exemplary embodiment of the present specification, the catalyst of Chemical Formula is an amidine-based ionic liquid catalyst.

According to an exemplary embodiment of the present specification, the method for preparing an asymmetric linear carbonate does not include a solvent (solvent free).

According to a preparation method in the related art, since two types of linear carbonates and an alcohol-based solvent are used, the preparation process is complicated, and the alcohol-based solvent is used to obtain at least five types of mixtures including a final target compound, so that a purification process for obtaining an asymmetric linear carbonate, which is a final target, is very complicated.

According to an exemplary embodiment of the present specification, since the method for preparing an asymmetric linear carbonate is performed while all of a first symmetric linear carbonate, a second symmetric linear carbonate and the catalyst of Chemical Formula 1, which take part in a transesterification reaction, are liquid materials and homogeneously mixed without using a solvent such as an alcohol-based solvent, a separate solvent is not needed, so that the process is simple, and after the reaction is completed, a first symmetric linear carbonate, a second symmetric linear carbonate and a final target asymmetric linear carbonate, which are a mixture of three types, are only produced, and thus the product is easily isolated and purified, costs for the process are low, and the resulting first symmetric linear carbonate and second symmetric linear carbonate can be used again in the process of preparing the asymmetric linear carbonate, and thus the method for preparing an asymmetric linear carbonate is very economical compared to the method in the related art.

According to an exemplary embodiment of the specification, the mixture of three types may be isolated and purified through fractional distillation using a difference in boiling points.

According to an exemplary embodiment of the present specification, the first symmetric linear carbonate is dimethyl carbonate (DMC).

According to an exemplary embodiment of the present specification, the second symmetric linear carbonate is diethyl carbonate (DEC).

According to an exemplary embodiment of the present specification, the temperature of the transesterification reaction is 80° C. to 120° C., preferably 90° C. to 100° C., and more preferably 95° C. to 100° C.

When the reaction is performed at the reaction temperature, the first symmetric linear carbonate and the transesterification rate of the second symmetric linear carbonate are optimized and the yield of the asymmetric linear carbonate is excellent.

According to an exemplary embodiment of the present specification, the transesterification reaction is a closed system reaction. The closed system reaction is a physical system that exchanges only energy without exchanging materials with the outside, and the transesterification reaction is performed using only the first symmetric linear carbonate, the second symmetric linear carbonate and the catalyst represented by Chemical Formula 1 without the inflow of external materials.

In the present specification, the alkyl group is straight-chained or branched, and the number of carbon atoms of the alkyl group is 1 to 4. Specific examples of the alkyl group may be a methyl group, an ethyl group, an n-propyl group, an isopropyl group, an n-butyl group, an isobutyl group, a tert-butyl group and the like.

According to an exemplary embodiment of the present specification, R1 is hydrogen, and R2 and R3 are the same as or different from each other, and are each independently hydrogen; a methyl group; or an isopropyl group.

According to an exemplary embodiment of the present specification, the catalyst represented by Chemical Formula 1 is any one selected among the following compounds.

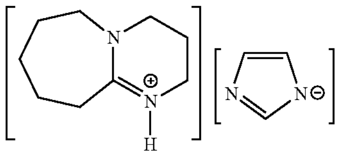

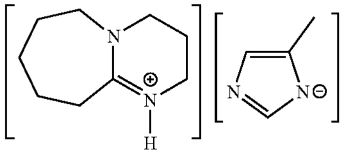

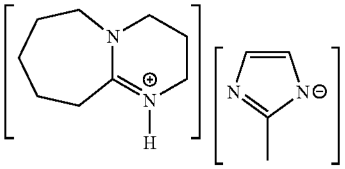

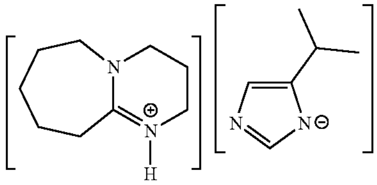

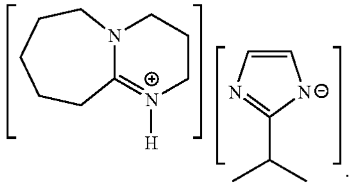

According to an exemplary embodiment of the present specification, the asymmetric linear carbonate is ethyl methyl carbonate (EMC).

According to an exemplary embodiment of the present specification, the asymmetric linear carbonate may be used as an electrolytic solution for a lithium secondary battery.

Hereinafter, the present specification will be described in detail with reference to Examples for specifically describing the present specification. However, the Examples according to the present specification may be modified in various forms, and it is not interpreted that the scope of the present specification is limited to the Examples described below in detail.

The Examples of the present specification are provided to more clearly describe the present specification to a person with ordinary skill in the art.

Synthesis Example 1. Preparation of Compound 1

0.6 g of imidazole and 1.5 g of 1,8-diazabicyclo(5.4.0)undec-7-ene were put into a 20-ml vial, and the resulting mixture was stirred at room temperature for 5 hours. When the reaction was completed, Compound 1, which is a pale yellow liquid, was obtained.

Compound 1

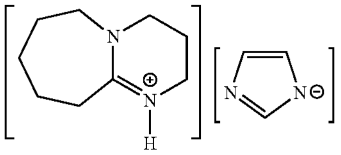

Synthesis Example 2. Preparation of Compound 2

Compound 2 was obtained by synthesis in the same manner as in Synthesis Example 1, except that 0.8 g of 2-methyl-1H-imidazole was used instead of imidazole.

Compound 2

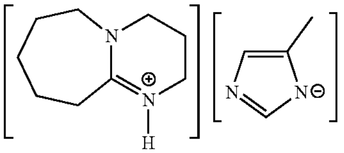

Synthesis Example 3. Preparation of Compound 3

Compound 3 was obtained by synthesis in the same manner as in Synthesis Example 1, except that 0.8 g of 4-methyl-1H-imidazole was used instead of imidazole.

Compound 3

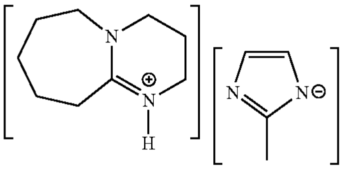

Synthesis Example 4. Preparation of Compound 4

Compound 4 was obtained by synthesis in the same manner as in Synthesis Example 1, except that 1.1 g of 2-isopropyl-1H-imidazole was used instead of imidazole.

Compound 4

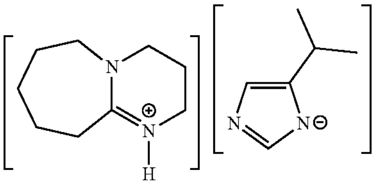

Synthesis Example 5. Preparation of Compound 5

Compound 5 was obtained by synthesis in the same manner as in Synthesis Example 1, except that 1.1 g of 4-isopropyl-1H-imidazole was used instead of imidazole.

Compound 5

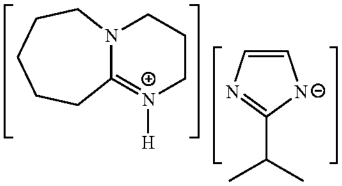

Experimental Examples. Preparation of Ethyl Methyl Carbonate

Example 1

10 g of dimethyl carbonate (DMC), 13.1 g of diethyl carbonate (DEC) (DMC:DEC=1:1, molar ratio) and 1 wt % of Compound 1 (DMC standard 1 wt %) as a catalyst were put into a 100-mL pressure reactor. The temperature was increased to 90° C. to 100° C., and the reaction was performed under stirring for 4 hours. When the reaction was completed, a gas chromatography (GC) analysis was performed by performing sampling.

The reaction was performed in a closed system, and additional pressure was not applied.

The reaction is performed as shown in the following Reaction Scheme 1, and no product is produced other than the three types of materials.

[Reaction Scheme 1]

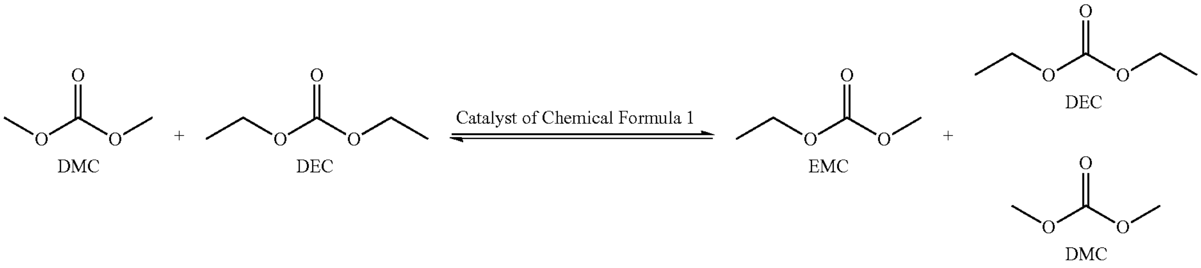

Example 2

The reaction was performed in the same manner as in Example 1, except that as the catalyst, Compound 2 was used instead of Compound 1.

Example 3

The reaction was performed in the same manner as in Example 1, except that as the catalyst, Compound 3 was used instead of Compound 1.

Example 4

The reaction was performed in the same manner as in Example 1, except that as the catalyst, Compound 4 was used instead of Compound 1.

Example 5

The reaction was performed in the same manner as in Example 1, except that as the catalyst, Compound 5 was used instead of Compound 1.

Comparative Example 1

Dimethyl carbonate (DMC) (10 g), ethanol (EtOH) (5.1 g) (DMC:EtOH=1:1, molar ratio) and 1 wt % (DMC standard 1 wt %) of sodium ethoxide as a catalyst were put into a 100-mL pressure reactor. The temperature was increased to 90° C. to 100° C., and the reaction was performed under stirring for 4 hours. When the reaction was completed, a GC analysis was performed by performing sampling.

The results of GC analysis of the materials prepared by the preparation methods of Examples 1 to 5 and Comparative Example 1 are shown in the following Table 1.

TABLE 1

| | Before reaction (mole %) | | After reaction (mole %) | | | | |
|---|---|---|---|---|---|---|---|
| | DMC | DEC | DMC | EMC | DEC | | |
| Example 1 | | 50 | 23.1 | 51.2 | 25.7 | | |
| Example 2 | | | 23.0 | 50.9 | 26.1 | | |
| Example 3 | 50 | | 24.0 | 50.5 | 25.5 | | |
| Example 4 | | | 23.7 | 50.8 | 25.5 | | |
| Example 5 | | | 22.8 | 51.1 | 26.1 | | |
| | DMC | EtOH | DMC | EMC | DEC | MeOH | EtOH |
| Comparative Example 1 | 50 | 50 | 22.4 | 22.8 | 5.7 | 38.9 | 10.1 |

DMC: Dimethyl carbonate
DEC: Diethyl carbonate
EMC: Ethylmethyl carbonate
MeOH: Methanol
EtOH: Ethanol In Table 1, in Comparative Example 1 using an alcohol-based solvent which is a method in the related art, a mixture of 5 types including EMC which is a final target is produced, so that it is difficult to isolate and purify the EMC.

In contrast, since the preparation method according to an exemplary embodiment of the present specification is performed while all of a first symmetric linear carbonate, a second symmetric linear carbonate and the catalyst of Chemical Formula 1, which take part in a transesterification reaction, are liquid materials and homogeneously mixed without using a solvent such as an alcohol-based solvent, a separate solvent is not needed, so that the process is simple. Furthermore, after the reaction was completed, DMC, DEC and a final target EMC, which are a mixture of three types, were only produced, the EMC is easily isolated and purified, costs for the process are low, and DMC and DEC can also be used again for the process of preparing an asymmetric linear carbonate, so that it could be seen that the preparation method according to an exemplary embodiment of the present specification is very economical compared to methods in the related art.

The invention claimed is:

1. A method for preparing an asymmetric linear carbonate, the method comprising: transesterifying a first symmetric linear carbonate and a second symmetric linear carbonate under a catalyst represented by Chemical Formula 1:

[Chemical Formula 1]

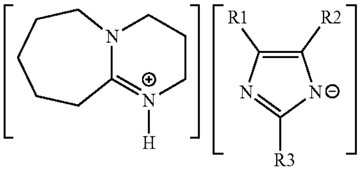

wherein, in Chemical Formula 1,

R1 to R3 are the same as or different from each other, and are each independently hydrogen; or a straight-chained or branched alkyl group having 1 to 4 carbon atoms, and at least one of R1 to R3 is a straight-chained or branched alkyl group having 1 to 4 carbon atoms.

2. The method for preparing an asymmetric linear carbonate of claim 1, wherein the method does not use a solvent.

3. The method for preparing an asymmetric linear carbonate of claim 1, wherein the first symmetric linear carbonate is dimethyl carbonate (DMC).

4. The method for preparing an asymmetric linear carbonate of claim 1, wherein the second symmetric linear carbonate is diethyl carbonate (DEC).

5. The method for preparing an asymmetric linear carbonate of claim 1, wherein the transesterification reaction is performed at a temperature of 80° C. to 120° C.

6. The method for preparing an asymmetric linear carbonate of claim 1, wherein R1 is hydrogen, and R2 and R3 are the same as or different from each other, and are each independently hydrogen; a methyl group; or an isopropyl group.

7. The method for preparing an asymmetric linear carbonate of claim 1, wherein the catalyst represented by Chemical Formula 1 is any one selected among from the following compounds:

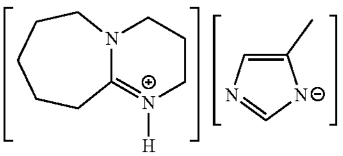

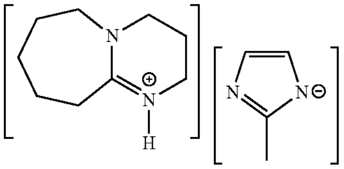

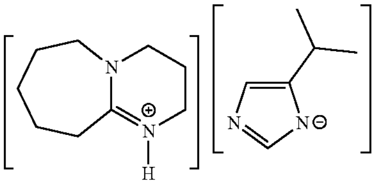

-continued
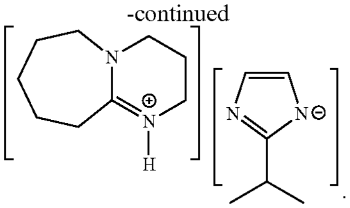
8. The method for preparing an asymmetric linear carbonate of claim 1, wherein the asymmetric linear carbonate is ethyl methyl carbonate (EMC).
* * * * *